United States Patent
Bundschus et al.

(10) Patent No.: US 8,560,346 B2
(45) Date of Patent: Oct. 15, 2013

(54) SYSTEM AND METHOD FOR RANKING QUALITY IMPROVEMENT FACTORS IN PATIENT CARE

(75) Inventors: Markus Bundschus, München (DE); Balaji Krishnapuram, King of Prussia, PA (US); Farbod Rahmanian, Leesport, PA (US); R. Bharat Rao, Berwyn, PA (US); Romer E. Rosales, Downingtown, PA (US); Shipeng Yu, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 660 days.

(21) Appl. No.: 12/634,878

(22) Filed: Dec. 10, 2009

(65) Prior Publication Data

US 2010/0174557 A1    Jul. 8, 2010

Related U.S. Application Data

(60) Provisional application No. 61/142,454, filed on Jan. 5, 2009.

(51) Int. Cl.
  *G06Q 50/00* (2012.01)
  *G06Q 10/00* (2012.01)
(52) U.S. Cl.
  USPC .................................................. 705/3; 705/2
(58) Field of Classification Search
  USPC ....................................................... 705/2–3
  See application file for complete search history.

(56) References Cited

U.S. PATENT DOCUMENTS

| | | | |
|---|---|---|---|
| 5,652,842 A * | 7/1997 | Siegrist et al. | 705/2 |
| 2002/0111826 A1* | 8/2002 | Potter et al. | 705/2 |
| 2003/0126101 A1 | 7/2003 | Rao et al. | |
| 2005/0289092 A1* | 12/2005 | Sumner et al. | 706/46 |

OTHER PUBLICATIONS

Morales, Hospital mortality rate and length of stay in patients admitted at night to the intensive care unit, Crit Care Med 2003 vol. 31, No. 3.*
CareDiscovery Quality Measures, Healthcare, Thomson Reuters, as of Nov. 24, 2009.
CareDiscovery Quality Measures, Healthcare, Thomson Reuters, http://thomasreuters.com/products_services/healthcare/healthcare_products/hosp_health . . . Nov. 25, 2009.
Statit piMD, CQI: "Measure, Monitor, Optimize. STAT-it!", MIDAS+ Statit Solutions Group, http://www.statit.com/statitpimd/index.shtml, Nov. 25, 2009.
Data Drives 'Perfect Care', Healthcare, Thomson Reuters Case Study, Clinical Performance Improvement, St. Joseph Medical Center, Reading, PA, 2008.

(Continued)

*Primary Examiner* — Tran Nguyen
(74) *Attorney, Agent, or Firm* — Joshua B Ryan (57) ABSTRACT

Quality improvement factors in patient care are ranked. Hospital performance is measured, such as a CMS measure. The variables and/or values relative contribution to quality of care is determined using medical records of the hospital. The variables and/or values are ranked according influence of the quality of care result. The ranking is performed by a given medical institution at a desired time rather than based on a broad study. The medical institution may regularly determine variables (e.g., admitting doctor) and/or values (e.g., doctor X) that are relevant to a decreased quality of care. Quality may be regularly improved using a software product.

17 Claims, 5 Drawing Sheets

(56) References Cited

OTHER PUBLICATIONS

Statit piMD, "Let Statit solutions and support personnel help you move from a manual, labor-intensive and costly process to automated, timely and effective performance improvement reporting", MIDAS+ Statit Solutions Group, Corvallis Oregon, Nov. 25, 2008.

Statit Quality Control First Aid Kit, "Introduction to Continuous Quality Improvement Techniques for Healthcare Process Improvement", Corvallis, OR, 2007, pp. iii-44.

Healthmark Software Solutions, 2006 ©, http://healthmarx.com/pages/Products.htm, Nov. 25, 2009.

O'Brien, Jennings, Bellin Health: "Living Quality Improvement Everyday" MIDAS Statit Solutions Group, Nov. 25, 2009.

\* cited by examiner

| VARIABLES INVOLVING STAFF | VARIABLES INVOLVING TIME | OTHER |
|---|---|---|
| ADMITTING DOCTOR<br>ATTENDING DOCTOR<br>REFERRING DOCTOR<br>NURSE STATUS<br>⋮ | DURATION OF STAY<br>ADMISSION TIME<br>DISCHARGE TIME<br>⋮ | AGE OF PATIENT<br>HOSPITAL SERVICE<br>PATIENT TYPE<br>PATIENT STATUS CODE<br>INSURANCE<br>ADMITTING DIAGNOSIS<br>⋮ |

SYSTEM AND METHOD FOR RANKING QUALITY IMPROVEMENT FACTORS IN PATIENT CARE

RELATED APPLICATIONS

The present patent document claims the benefit of the filing date under 35 U.S.C. §119(e) of Provisional U.S. Patent Application Ser. No. 61/142,454, filed Jan. 5, 2009, which is hereby incorporated by reference.

BACKGROUND

The present embodiments relate to quality improvement in patient care. In particular, areas for improving patient care at a medical institutions are identified.

During treatment of patients, hospitals collect considerable amounts of information related to patient care. The collected data includes basic information, such as the date and time of visit/admission, patient age, attending doctor, responsible nurse(s), admitting hospital unit, department that provided the service(s), billing code, and many other variables. The data may also include more detailed information, such as patient symptoms, medications administered, and procedures performed. The data is stored as structured or unstructured data in a computerized patient medical record. This computerized medical record includes the variables and/or values for the variables. Hospitals generally maintain records of these variables and values for a large collection of patients.

Healthcare institutions measure their quality of care using predefined criteria. Often, the criteria are based on whether specific events or processes were followed during patient care. In many instances, the identification of such events requires chart abstraction or analysis. The chart information is examined to determine whether the events or processes occurred during treatment of a given patient. Chart abstraction is a time consuming manual process.

Automated chart abstraction may be provided. For example, the Soarian® Quality Measures program manages and facilitates automatic chart abstraction. The computerized patient record (e.g., structured defined data fields and/or unstructured text or images) is mined to determine whether the events occurred and/or were documented. A score is determined based on the number of patients for which the required events occurred and did not occur (likewise were documented or no). The computerized patient record is also mined to gather and process information. Example of information that is gathered includes discharge medications (e.g.; drug name and dosage), patient admission/arrival date and time, patient surgery date and time, attending physician, admission diagnosis, admitting hospital unit, patient condition, medical procedures applied, etc.

The quality of care indicates overall performance by the hospital for a condition. Where a hospital desires to improve the quality of care, the quality of care measurements may indicate in what measures/care elements the hospital is failing more or failing less, but provides little guidance on how to improve the quality of care.

SUMMARY

In various embodiments, systems, methods, instructions, and computer readable media are provided for ranking quality improvement factors in patient care. The variables and/or values relative contribution to quality of care is determined. The variables and/or values are ranked according influence of the quality of care result. The ranking is performed by a given medical institution at a desired time rather than based on a broad study. The medical institution may regularly determine variables (e.g., admitting doctor) and/or values (e.g., doctor X) that are relevant to a decreased quality of care. Quality may be regularly improved using a software product rather than commissioning a study.

In a first aspect, a system for ranking quality improvement factors in patient care is provided. An input is configured to receive a user selection of a quality criteria for operation of a medical facility and to receive user activation, at the medical facility, of a statistical analysis of the quality criteria. A computer readable media has stored therein values for a plurality of variables associated with care of a plurality of patients treated at the medical facility and a pass/fail score for the quality criteria of each of the patients. A processor is configured to perform the statistical analysis, in response to the user activation, of the quality criteria as a function of the variables and values for the variables for the patients of the medical facility. The performance ranks the variables by relevance to the pass/fail scores across the patients of the medical facility. The performance ranks the values for each variable by relevance to the pass/fail scores across the patients of the medical facility. A display, at the medical facility, is configured to output an identification of at least a first one of the variables and at least one value for the first variable based on the ranking.

In a second aspect, a computer readable storage medium has stored therein data representing instructions executable by a programmed processor for ranking quality improvement factors in patient care. The instructions include identifying a plurality of factors and an attribute for each of the factors for each of a plurality of patients in a computerized medical record, the factors comprising data fields in the computerized medical record for which the attributes are stored for each of the patients; identifying scores of a measurement of success for the patients; determining statistics for each attribute for each of the factors as a function of the scores of the measurements of success; ranking the factors as a function of the statistics; outputting a first factor of the factors as a function of the rank; and interacting with a user to perform the identifying instructions, determining instruction, rank instruction and output instruction in response to a request from the user for quality improvement analysis for the measurement of success, a plurality of different measurements of success being available to analyze.

In a third aspect, a method is provided for ranking quality improvement factors in patient care. A computer readable media product is generated. The computer readable media product has instructions executable by a programmed processor for measuring effect of different values in different fields of a computerized medical record of a medical institution to a success rate of each of a plurality of different quality criteria. The different quality criteria are for measuring performance of the medical institution in different medical conditions. The instructions also are for outputting the measured effect for at least a first one of the different values. The first one of the different values is output as a function of a relative level of the effect as compared to other values. The computer readable media product is distributed to a plurality of medical institutions for application to the computerized medical record of each of the medical institutions as a function of the quality criteria for the respective medical institution. Different medical institutions have different success rates for the quality criteria and different computerized medical records.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Hospital factors that are relevant to quality improvement (QI) are identified, ranked, and displayed. The factors of interest are those related to patient care in some way, even if not intuitively. Factors denote elements that can affect quality, including clinical variables, events, people, patient information, billing, or processes involved in patient care. Examples of factors related to patient care include patient arrival time, attending doctor, admitting hospital unit, patient condition, medical procedures applied, and diagnoses. A variable can be predefined as a field in a data repository (e.g., "Admission Time" or "Admission Doctor"), a combination of several available fields (e.g., "Admission Time" and "Admission Doctor"), or derived based on the available information about this patient (e.g., the "Smoking History" based on the freetext patient records). An attribute is a possible value in one variable, such as a specific time range in the variable "Admission Time," or a certain doctor in the variable "Admission Doctor."

Given a particular measure of success (e.g., a measure of quality) in patient care, it is valuable to identify the factors or attributes that are most important for achieving success or high quality in patient care. Examples of quality measures include Patient Safety Indicators, Inpatient Quality Indicators, Pediatric Quality Indicators, Prevention Quality Indicators defined by the Agency for Healthcare Research and Quality (AHRQ), or those defined by the Centers for Medicare and Medicaid Services (CMS) and the Joint Commission on the Accreditation of Healthcare Organizations (JCAHO). Other examples of quality measures include those identified by: Agency for Healthcare Research & Quality (AHRQ), Administration on Aging (AoA), Centers for Disease Control and Prevention (CDC), Centers for Medicare & Medicaid Services (CMS), Health Resources and Services Administration (HRSA), Indian Health Service (IHS), National Institutes of Health (NIH), Office of the National Coordinator for Health Information Technology (ONC), Office of Public Health and Science (OPHS), and Substance Abuse and Mental Health Services Administration (SAMHSA).

Given a number of factors and a measure of quality, a rating (e.g., a relevance score) is assigned to each factor. A ranked list of such factors may be created in order of relevance. The identified and/or ranked list of factors is displayed. Alternatively, for each factor (e.g., patient arrival time), the relevant attributes for the factor can be further identified or ranked (e.g., a ranked list of arrival periods). The relevance can be defined in terms of various criteria.

For quality improvement purposes, variable ranking indicates the most relevant variables (e.g., to see if "Admission Time" is more relevant for quality improvement than "Admission Doctors"), and attribute ranking indicates which specific attribute within a variable is mostly relevant. The variables and values may not even be used for determining the quality score or criterion. The uses of this information are very large: a relevance score for each factor can show how important the factor is at improving the measure of quality, and a ranked list of factors can help in improving patient care in general, supporting decision making and easing and accelerating analysis of processes. For example, under performing or better performing doctors, nurses, departments, shifts, or other aspects may be identified to assist in allocating resources to improve patient care.

In one embodiment, a function is added to a program for reporting quality scores. The function provides guidance, such as hints, impressions, or direct feedback, about where or in what way the hospital fails or succeeds. For core measures, an indication is provided as to why the hospital fails in some cases. If a failure rate increases or is not at a desired level, helpful information may be provided by the function on demand and without commissioning a study. Hospital administrators may more easily detect possible improvements in processes and/or personnel.

Figure 1:
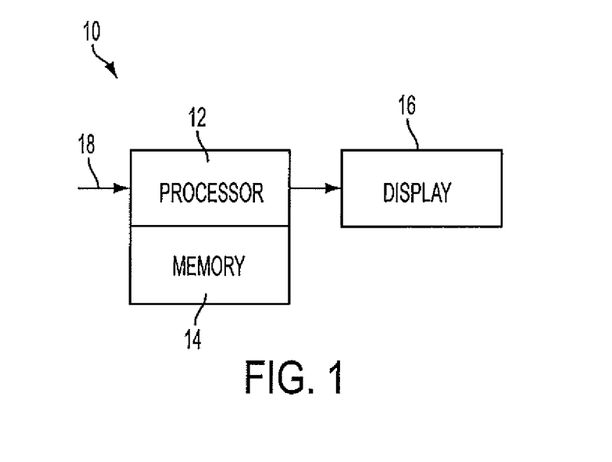
FIG. 1 is a block diagram of one embodiment of a system for ranking quality improvement factors in patient care.

FIG. 1 shows a block diagram of an example system 10 for ranking quality improvement factors in patient care. The system 10 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated or automated workflows are provided to assist a user in identifying variables or values of variables most relevant to quality scores. Areas of focus in improving patient care as measured by quality scores may be determined, such as identifying times of admission or physicians that perform relatively well or poorly with respect to a quality criterion. For example, the morning shift (values of the time of admittance variable) and nursing staff (variable) are identified as benefiting from training regarding pneumonia patient treatment in order to improve PN-1 scores from CMS.

The system 10 is a computer, personal computer, server, PACS workstation, imaging system, medical system, network processor, network, server, or other now known or later developed processing system. The system 10 includes at least one processor (hereinafter processor) 12, at least one memory (hereinafter memory) 14, a display 16, and at least one input (hereinafter input) 18. The processor 12 is implemented on a computer platform having hardware components. The computer platform may also include an operating system and microinstruction code. The various processes, methods, acts, and functions described herein may be either part of the microinstruction code or part of a program (or combination thereof) executed via the operating system. Additional, different, or fewer components may be provided.

The input 18 is a user input, network interface, external storage, or other input device configured to provide data to the system 10. The configuration is through control, software, and/or hardware. For example, the input 18 is a mouse, keyboard, track ball, touch screen, joystick, touch pad, buttons, knobs, sliders, combinations thereof, or other now known or later developed user input device. The user input 18 may operate as part of a user interface. For example, one or more buttons are displayed on the display 16. The user input 18 is used to control a pointer for selection and activation of the functions associated with the buttons. Alternatively, hard coded or fixed buttons may be used. As another example, the input 18 is a hard-wired or wireless network interface. A universal asynchronous receiver/transmitter (UART), a parallel digital interface, a software interface, Ethernet, or any combination of known or later developed software and hardware interfaces may be used. The network interface may be linked to various types of networks, including a local area network (LAN), a wide area network (WAN), an intranet, a virtual private network (VPN), and the Internet. The network interface may be linked to the memory 14 or other memory, such as a database of values associated with variables for patients.

In one example embodiment, user navigation options for viewing and selecting the statistics, the measurements of success, the factors, the attributes of the factors, and/or rankings are presented to the user. User selection of one of the quality measures is received. In response to selection of the quality measure, one or more factors (e.g., variables) and/or attributes (e.g., values of variables) are output as having a highest relevance with the selected quality measure.

The input 18 is an interface to receive a user selection of a quality criterion for operation of a medical facility. For example, the user selects a quality criterion for performing a quality measure, for identifying a variable or value for quality improvement, or both. The selection may be to perform currently or based on past performance of a quality scoring algorithm. In addition to or as an alternative to performing the quality scoring, the user activates statistical analysis of the quality criteria. The activation may be direct, such as the user selecting the process for performance at the time of selection. Alternatively, the activation is to configure for regular, periodic, or performance at other times (e.g., performance in response to any determination of a quality score). In other embodiments, the processor 12 automatically selects a quality criterion or criteria, such as based on an insufficient score.

The user or processor activation is at the medical facility. The user input 18 is at the same hospital, practice, or medical group (e.g., group of affiliated hospitals or physicians). An administrator or other at the medical facility, seeking to improve patient care for the medical facility, activates the statistical analysis. The user input 18 may be remote from the processor 12, such as where the processor is operated by another. The user input 18 and/or the display 16 are local or in a same medical facility being analyzed.

Alternatively, the user input 18 and/or display 16 are remote from the facility but operated by a member of the medical facility, such as an administrator activating the analysis from a home computer. In yet other embodiments, a third party service activates and performs the analysis on a regular basis for the particular medical facility. Analysis may also be performed for groups of medical facilities.

The statistical analysis and a user interface for receiving the user activation and causing the display of the identification are provided as a product. Rather than commissioning a study by researchers for a particular medical facility or relying on studies at other medical facilities, personnel at the medical facility may acquire the product and use statistical analysis related to quality criteria for quality improvement on an ongoing basis for the specific medical facility. Any entity (medical facility) for which quality criteria is reported to another organization may use the product to improve performance of medical services. The medical facility may run the product for internal quality criteria.

The user input 18 is part of a user interface for interacting with a user to perform the statistical analysis. The user interface allows a user to identify one or more possible variables or values of interest. The available variables are selected for inclusion or exclusion in the statistical analysis. In other embodiments, the variables and/or values of interest are pre-programmed or based on the database of the medical facility (e.g., all available variables). The user interface allows a user to determine one or more quality scores of interest. In other embodiments, the quality scores are selected automatically (e.g., poor results) or for any quality scoring performed. The user interface allows a user to select a rank or rank format. In other embodiments, ranking is automatically performed and/or provided in a predetermined format. The user interface allows a user to select an output or output format. In other embodiments, the output or output format is automatically determined or in a predetermined arrangement. The selections for activation, operation, and/or display are provided in response to a request from the user for quality improvement analysis for the one or more measurements of success.

Figure 2:
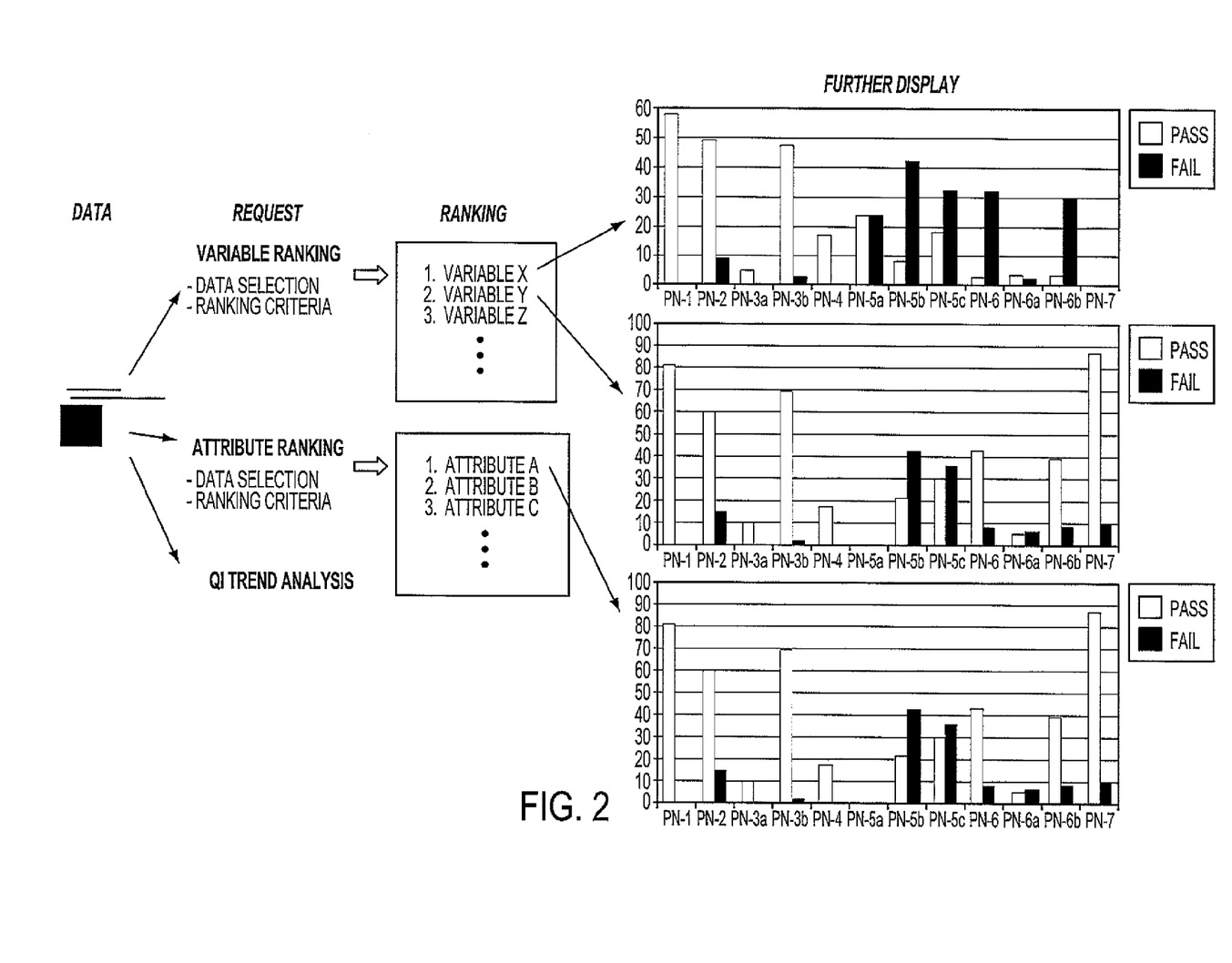
FIG. 2 is a graphical representation of user navigation levels for ranking quality improvement factors.

The output may provide useful information to a user. The user interface may allow the user to navigate through associated information. For example, the user can select a variable or attribute based on computed statistics to further investigate the results. The statistics, factors, quality scores, and attributes are linked together in the user interface so that display of one may allow selection and display of corresponding information. For example, FIG. 2 is an illustration of various stages of the user interaction with the quality improvement system. A selection in one stage may result in related information in another stage being available to the user for the current analysis. For example, the user first sees a data screen with detailed statistical information (e.g., pass/fail counts or rates) for each core measure (e.g., quality score) or a selected core measure. Alternatively, the user sees a list of core measure results. When the user chooses to work on quality improvement (e.g., selecting a quality improvement button for example), the user has the options to do variable ranking, attribute ranking or some other advanced analysis (such as trend analysis across time). The data/variable/attribute options are displayed and the ranking criterion can be selected. Alternatively, a predetermined ranking criterion is used. The system then shows a list of variables and/or attributes depending on the configured options. When the user chooses one of the variables and/or attributes, a detailed histogram, chart or table display can be shown to help the user understand the performance or relationship of a given variable or value to the quality score. Other user interfaces may be provided.

The user interface and associated information are provided retrospectively. The data is gathered and analyzed as part of scoring after treatment of one or more patients. For example, the quality scoring is performed periodically (e.g., once a quarter or annually). The statistical analysis for quality improvement is performed as part of the scoring or after scoring. In other embodiments, the user interface and associated information are provided during treatment or within hours or days of treatment of one or more patients. More immediate feedback or feedback during treatment may assist in avoiding problems with scoring to be performed later. For example, a supervisor may be informed that a physician with high correlation to poor performance in a quality measure is treating a patient for the measured condition. The supervisor may more likely guide the physician to avoid failures for the condition.

Referring again to FIG. 1, the memory 14 is a computer readable storage medium having stored therein data representing instructions executable by the programmed processor 12 for ranking quality improvement factors in patient care. The processor 12 is configured pursuant to instructions. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The memory 14 alternatively or additionally stores therein values for a plurality of variables. The same or different computer readable media may be used for the instructions, patient data, statistics, and quality scores. The patient records are stored in an external storage, but may be in other memories. The external storage or the memory 14 may be implemented using a database management system (DBMS) managed by the processor 12 and residing on a memory, such as a hard disk, RAM, or removable media. The memory 14 is a computerized patient record system, such as a data warehouse system residing on a separate computer system, a PACS system, or any other now known or later developed hospital, medical institution, medical office, testing facility, pharmacy or other medical patient record storage system. The patient record data may be distributed among multiple storage devices.

The variables are data fields associated with care of a plurality of patients treated at the medical facility. These factors are part of a structured database. Different medical facilities may have different variables in their database. The variables may be part of different systems, such as separate diagnosis and drug databases. Alternatively, the variables are compiled into a single database. The values for the variables are stored for each patient in a same database or different databases. For each patient, a patient specific value is provided for each or a sub-set of the variables. One or more values and/or variables may not be available for a given patient.

The values may be stored as part of the structured database or databases, or stored in an unstructured format, such as in free text (e.g., physician notes) or images (e.g., DICOM images). The values used for statistical analysis may be mined and stored in a structured format for statistical analysis. For example, the mining from structured and/or unstructured data disclosed in U.S. Published Application Serial No. 2003/0126101 is used to determine values for one or more variables. For example, possible values are determined from structured and/or unstructured sources. The possible values may be determined from the unstructured sources by image processing and/or natural language processes. Based on probabilistic combination, the value for a given variable is inferred from the evidence gathered from structured and/or unstructured data sources. Other sources or techniques for determining the values of the variables may be used.

The database includes values for the variables of a plurality of patients treated at the medical facility. The database is or includes the patient records of the medical facility, such as patient records for patients used to determine a quality score. The patient records are not for other patients, such as not including patients of other medical facilities. In other embodiments, the medical record may include other such patients, such as being a collection from a plurality of related or unrelated medical facilities.

The memory 14 or other memory can store the quality scores and/or data used to derive the quality scores. For example, a pass/fail score (e.g., passed or failed) is stored for each patient in a group of patients qualifying to be included in the quality score. The overall pass/fail ratio is stored with or without the individual patient scores as well. Other scoring may be used and stored, such as numerical scores. Scores are provided for one or more quality criteria, such scores for hundreds of criteria.

The processor 12 has any suitable architecture, such as a general processor, central processing unit, digital signal processor, server, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 12. The processor 12 implements the program alone or includes multiple processors in a network or system for parallel or sequential processing. The processor 12 is configured by the program or by design to perform the functions, acts, or processes described herein.

The processor 12 is configured by software and/or hardware to identify a plurality of factors and an attribute for each of the factors for each of a plurality of patients in a computerized medical record. For example, the processor 12 is configured to interact with a computerized patient record. The variables and possible values available or selected in the patient record are identified by preprogramming and/or searching. For each medical facility, different variables and/or possible values (e.g., different groupings or value ranges) are available in the patient medical records. The processor 12 identifies the available or desired variables using this knowledge. Fewer than all available variables may be identified. For example, the variables identified are limited to selected or variables of interest for quality improvement. The user or program product may make assumptions about the variables of interest, only identifying variables potentially or likely to sufficiently be associated with quality improvement for a given quality criterion of interest. The processor 12 is programmed to access the computerized medical record for the identified variables, such as identifying data fields in the computerized medical record for which the attributes are stored for each of the patients or mining for the information.

Figure 3:
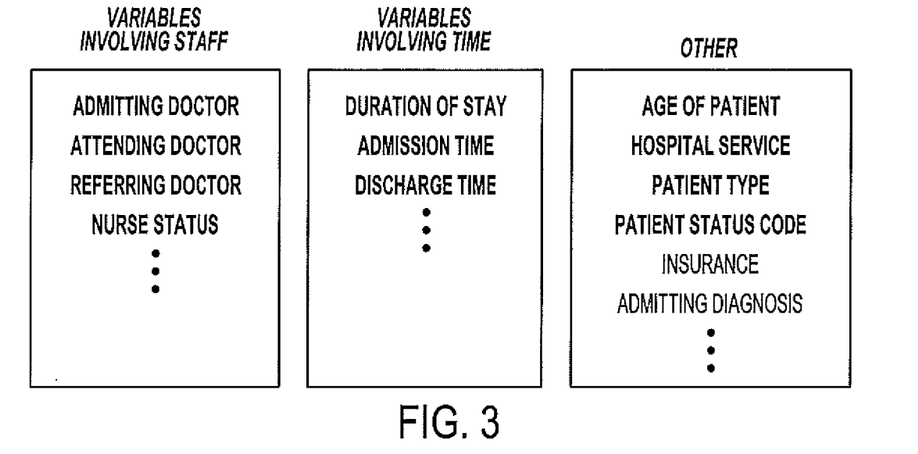
FIG. 3 is an example chart of variables in a computerized patient record.

A given medical facility may have a few, tens, hundreds, or other numbers of variables for each patient. For example, data fields or other factors include admitting physician, attending physician, referring physician, consulting physician, admission time, duration of stay, discharge time, age of patient, nurse status (e.g., type of nurse), patient type (e.g., emergency verses outpatient), patient status code, patient race, patient ethnic group, patient sex, patient admission diagnosis, hospital service or department, and other factors. FIG. 3 shows example factors divided amongst three groupings. No or different groupings may be provided. The factors are variables routinely tracked or recorded by a given medical facility, even if not recorded or tracked for determining the quality score. The factors may not be routine, such as mining for information not specifically tracked.

The attributes for each factor to be analyzed are also identified. The possible values for each variable are identified by preprogramming, user selection, and/or searching. For example, the attributes for each physician factor are the employee identification numbers for the physicians. As another example, the temporal factors (e.g., admission time, duration of stay, or discharge time) have attributes divided into specific ranges, such as hour or multi-hour increments. In yet another example, the hospital department factor has possible values specific to a given medical facility.

The processor 12 is configured to identify scores of a measurement of success for the patients. The scores are stored in memory 14 and/or created by the processor 12. For example, the scores may be automatically and/or manually generated and input. The processor 12 identifies the scores using knowledge, such as accessing scores reported for a given medical facility by preprogramming. As another example, one or more scores are identified by user selection. The user picks a given quality measure from a list of available quality measures. The user pick identifies the measure of success. The score associated with the selected measure is determined by mining, searching, and/or look-up operation.

Any measurement of success may be identified. In one embodiment, the quality measures from Centers for Medicare and Medicaid Services (CMS) or Joint Commission on the Accreditation of Healthcare Organizations (JCAHO) are provided. For example, the CMS core measure for community acquired pneumonia (CAP) quality initiative (PN-1) is identified. The measure of success is selected from the quality measures. Other core measures of quality, such as for other healthcare standards or organizations, may be used. Any measure of quality used by a given medical facility may be identified.

Figure 4:
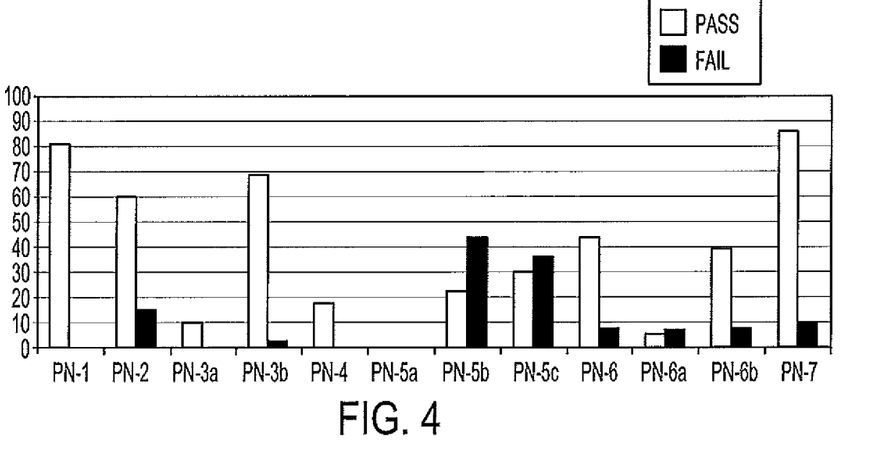
FIG. 4 is an example chart of pass/fail scores for quality criteria.

FIG. 4 shows example CMS core measures for a quarter of a year of an example medical facility. PN-1 is shown as one of the measures. In PN-1, the score is shown as pass if the pneumonia patient was documented as being a smoker or not in the previous year and documented as being instructed to cease smoking. FIGS. 5-8 are examples associated with identification of the PN-5b score. The PN-5b score is for pneumonia patients based on whether the patients receive their first dose of antibiotics within 4 hours after arrival at the hospital. Other examples are possible, such as left ventricular function (PN-2). For PN-2, the pass score depends on whether ejection fraction was measured and whether the patient was assessed for left ventricular function.

The identification may be focused or performed as a function of other information. For example, the available overall scores or quality measures are examined and the score with the highest fail rate or highest number of failures is identified. Multiple scores with higher fail rates or numbers of failures may be identified. As another example, one or more quality criteria with unexpected or any increase in failure from a previous measure may be identified. Scores associated with greater passing rates or numbers of passes may be identified, such as to determine a possible cause and reward or emulate the cause for other measures.

The processor 12 is configured to perform the statistical analysis. The analysis is performed in response to the user activation. The analysis is of the quality criteria as a function of the variables and values for the variables for the patients of the medical facility. The analysis is specific to the medical facility rather than being based on data from other facilities. The analysis may be repetitively performed for quality improvement on an ongoing basis specific to the scores of a medical facility rather than being extrapolated from study results of a onetime study and/or based on data at a different medical facility.

The statistics are determined for each identified attribute for each of the identified factors as a function of the identified measurements of success. The patient specific scores of each measurement are used to calculate the statistics. A separate analysis is performed for each of the measurements of success, based on the respective scores for each patient used for the measure of success.

Any statistical analysis may be used. In one embodiment, statistics are determined based on pass/fail scores. A histogram analysis of each variable for each core measures is determined. For example, a frequency table is generated. The frequency table indicates the number of pass and number of fail patients associated with each factor. The number of pass and number of fail patients associated with each attribute of each of the factors or a given factor may additionally or alternatively be determined.

The processor 12 is configured to rank the factors as a function of the statistics. By performing the statistical analysis, the variables may be ranked. The ranking indicates a relevance of the variable to the scores of the measurement of success. For example, the relevance of the variables to the pass/fail scores is determined across the patients of the medical facility. Any relevance function may be used. For example, a mutual information measurement, conditional entropy measurement, or both are used. In other examples, chi-square tests of independence, chi-square tests of goodness of fit, a median test, Fisher's test, or statistical deviance tests are used. The function ranks the variables automatically according to effect or other measure of interestingness of the variable to the score result. For example, admitting doctor may be found to have more influence on failure for PN-5b than the hospital service. The admitting doctor variable has a higher interestingness according to how much information the outcome (pass/fail) and the variable share.

In one embodiment, the ranking function is based on mutual information. The mutual information between the (e.g., pass/fail) outcome and the variable of interest is calculated. The function is given as:

$$I(X:Y) = \sum_{y \in Y} \sum_{x \in X} p(x, y) \log\left(\frac{p(x, y)}{p_1(x)p_2(y)}\right),$$

where I(X;Y) is the mutual information, x represents the variables to be ranked, and y represents the core measurements or per patient scores. The probability p(x,y) is determined from the frequency table, histogram analysis, or other statistical analysis. The marginal distribution in x is represented as $p_1(x)$, and the marginal distribution in y is represented as $p_2(y)$. The mutual information represents a degree of correlation. The result is an ordered list of variables by amount of mutual information. The variable with the greatest amount of mutual information is the highest ranked variable or variable with the greatest relevance.

In another embodiment, the ranking function is based on conditional entropy. The conditional entropy of the (e.g., pass/fail) outcome is calculated after observing the distribution of the variable of interest. The conditional entropy is represented as:

$$H(Y|X) \overset{def}{=} \sum_{x \in \chi} p(x) H(Y | X = x)$$
$$= -\sum_{x \in \chi} p(x) \sum_{y \in y} p(y|x) \log p(y|x)$$

wherein H(Y/X) is the conditional entropy. The conditional entropy represents how much an amount of uncertainty of the core measure y depends on the variable x.

The processor 12 ranks the attributes. The performance of the statistical analysis provides for ranking the values for each variable by relevance to the pass/fail scores across the measure relevant patients of the medical facility.

Any attribute ranking function may be used. For example, the ranking is based on a pass/fail ratio associated with each value or value range. The attribute level indicates an interestingness according to the ratio of fails and passes. The pass/fail ratio may be used in any desired calculation, such as weighting based on one or more considerations. In one embodiment, a smoothed fail rate rank is given as:

$$FR(a) = \frac{Fails_a + 1}{(Passes_a + Fails_a) + 2}$$

where a is the attribute. For example, a is a certain doctor, department, or time range. Fails, and Passes, are the numbers of failed and passed patients who have this attribute. Other attribute rankings may be used.

The ranking may be refined, such as using a variance-based penalty term for the smoothed failure rate. Attributes associated with a greater variance may have the attribute ranking reduced as compared to attributes with a lesser variance but similar ranking. One possible function is given as:

$$FRP(a) = FR(a) - c \sqrt{\frac{FR(a)(1 - FR(a))}{(Passes_a + Fails_a)}}$$

where c is a parameter to indicate the penalty level. c is selected by the user or set based on any criteria. For example, c=1.0.

The processor 12 may perform the statistical analysis in response to repeated user activations. Where the medical facility owns the software product or subscribes to the service, someone may perform the statistical analysis multiple times without commissioning studies. The statistical analysis may be performed for different quality criteria using the database of the medical facility. The performance is activated as desired or needed.

In one embodiment, further information is determined. The rankings may be plotted over time or a variance over time determined. A trend analysis may be performed. Variables or values associated with increasing rankings may indicate trends to be addressed for quality improvement of patient care. By providing for multiple activations of statistical analysis over time due to the convenient availability of the software, a trend may be determined.

The processor 12 outputs a ranked list of factors, a ranked list of attributes, a specific factor, a specific attribute, a graph, statistics, quality score, and/or other information. For example, the processor 12 outputs one or more of the display of FIGS. 2 and 4-8 or similar graphs, charts or tables for the same or different variables and/or values. The output is to the display 16, but may additionally or alternatively be to the memory 14 or a remote location.

The output and/or inputs may be displayed to a user on the display 16. The display 16 is a CRT, LCD, plasma, projector, monitor, printer, or other output device for showing data.

The display 16 is at the medical facility for which the quality improvement is being performed. Since the quality improvement is a product or available for use during scoring or regularly, the location of the display 16 is local. Alternatively, the display 16 is remote from the medical facility.

The display 16 is configured to display an image. The image may be of a medical image, a user interface, charts, graphs, values, or other information. For example, the display 16 generates an image of the output information from the processor 12. The processor 12 configures the display by generating display values for the image. The display is text, graphical, or other display.

In one embodiment, the image is an identification of at least one of the identified variables. For example, the variables are output as a function of the rank. A list of variables is output. The variables more closely related to failures of the quality scores are output or highlighted by order, color or other visual indicator. Alternatively, a highest ranked variable or variables are output, such as the variables most relevant to quality improvement. For example, a list of all the variables or a number (e.g., 10) of the variables most relevant to failure is generated from conditional entropy for the PN-5b measure as:

1. Referring Doctor
2. Admitting Doctor
3. Attending Doctor
4. Nurse Status
5. Duration of Stay
6. Admission Time 4 h (in 4 hour intervals)
7. Patient Type
8. Hospital Service
9. Patient Status Code
10. Admission Time 6 h (in 6 hour intervals)

The first variable, referring doctor, is associated with the highest number of failures, and/or greatest relevance (e.g., greatest conditional entropy). Other ordering may be used.

Other information associated with the factor may be displayed, such as supporting statistics. For example, the frequency table entries associated with the factor or factors are displayed. As another example, attributes with or without ranking information are displayed for one or more of the variables. Ranked lists of variables and respective value rankings are output together or linked in the user interface. In another example, the quality score with or without supporting abstracted information is displayed with the variable.

Figure 5:
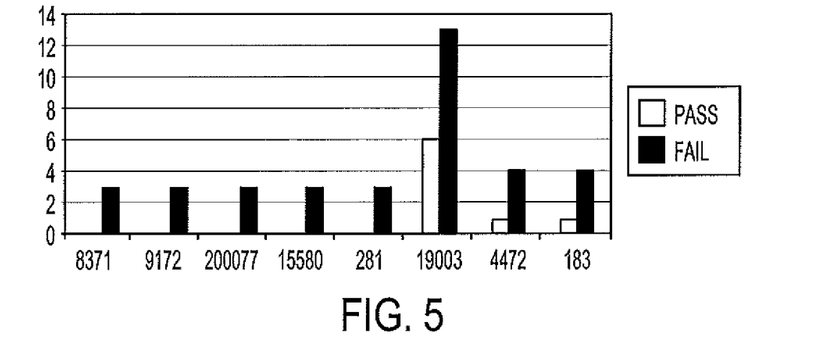
FIG. 5 is chart for the variable of referring doctor showing values associated with higher fail rates in one example.
Figure 6:
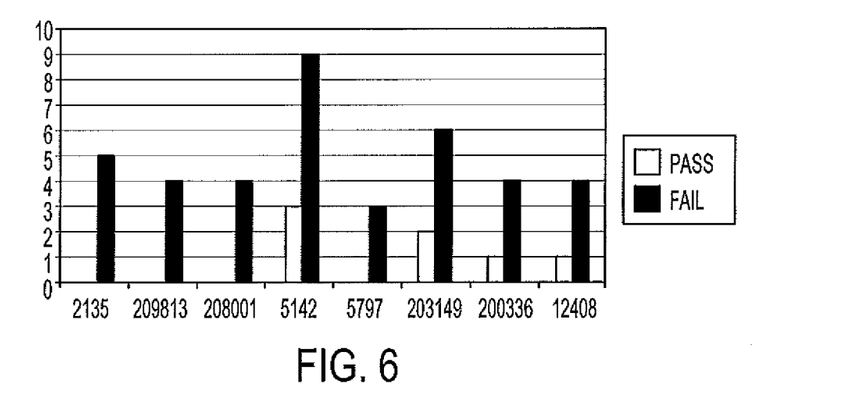
FIG. 6 is a chart for the variable of admitting doctor showing values associated with higher fail rates in one example.
Figure 7:
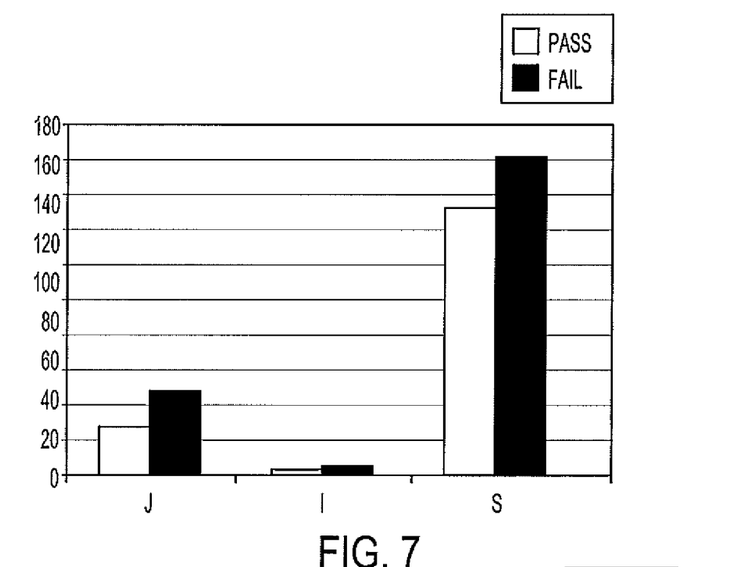
FIG. 7 is an example chart for the variable patient type showing values associated with higher fail rates.

FIG. 5 shows an example where the variable referring doctor has a high or highest relevance. The variable may be selected from a ranked list or output without selection as relevant for quality improvement. Further statistics are provided for the variable, such as the attributes with the highest relevance for this variable. A chart of the pass and fail scores by number of patients is given for the poorest performing physicians in referral. FIG. 6 shows a similar example, except for the admitting doctor variable. FIG. 7 shows another example for the patient type. More or less information may be provided, such as identifying a greater number of values and/or showing variables and/or values with the best pass rate.

In one embodiment, the image is an identification of one or more attributes. For example, the attributes are output as a function of the rank. A list of attributes and the corresponding pass/fail ratio, rates or other information is output. The values more closely related to failures of the quality scores may be output or highlighted. Alternatively, a highest ranked value or values are output. The values are for a selected factor regardless of factor rank or based on factor rank. The image may include all the possible attributes or a subset. For example, attribute rankings for admission times are shown in Tables 1 and 2.

TABLE 1

Attribute ranking for Factor Admission Time Based on fail rate rank:

| Atribute (value) | Fail rate score |
|---|---|
| 0-4 h | 0.6296296296296297 |
| 20-24 h | 0.60431654676259 |
| 12-16 h | 0.5882352941176471 |
| 8-12 h | 0.5625 |
| 16-20 h | 0.4752475247524752 |
| 4-8 h | 0.47368421052631576 |

TABLE 2

Attribute ranking for Factor Admission Time Based on penalized fail rate rank:

| Attribute (value) | Penalized fail rate rank |
|---|---|
| 20-24 h | 0.5625387143009406 |
| 0-4 h | 0.5330488532562571 |
| 12-16 h | 0.527655452877125 |
| 8-12 h | 0.471928895336316 |
| 16-20 h | 0.425057248925709 |
| 4-8 h | 0.352584475445152 |

The rate rank is the calculated relevance, but may be other information, such as mere ratio of passes or failures to the total number of patients associated with a given factor.

Figure 8:
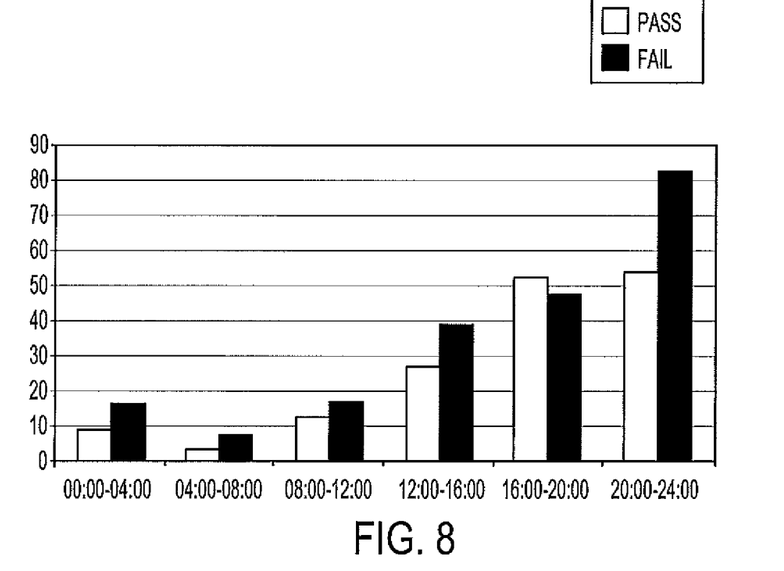
FIG. 8 is one example chart for the variable admission time showing ranking for all possible values.
Figure 9:
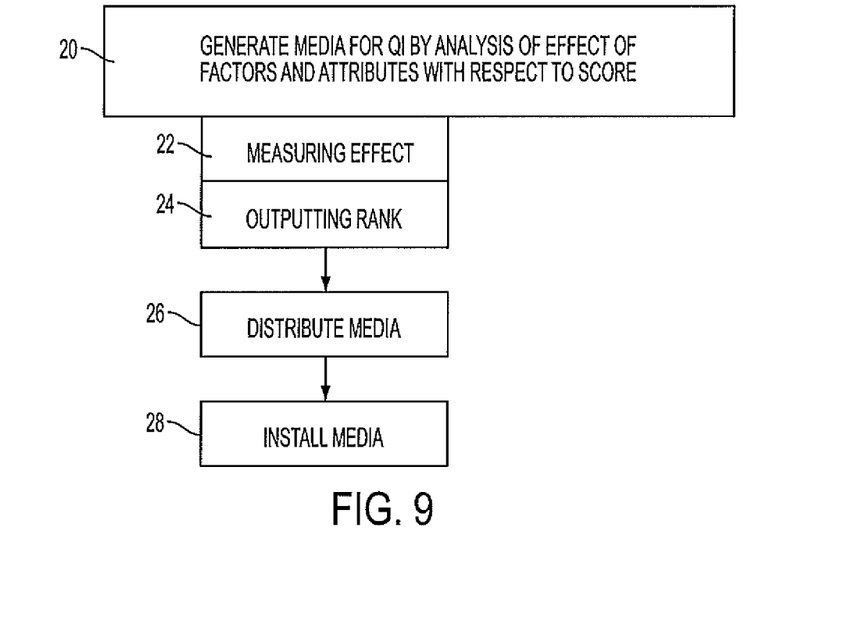
FIG. 9 is a flow chart diagram of one embodiment of a method for ranking quality improvement factors in patient care.

Associated information, such as statistics, quality score, and/or variable information may also be output with the attribute information. For example, FIG. 8 shows the admission time attributes with the pass/fail scores for each value.

Further processing may be performed by the processor 12. The relevance of combinations of factors and/or attributes is determined. For example, referring doctors (factor 1) who fail might usually give a wrong admitting diagnosis (factor 2). By calculated a combined relevance, stronger correlation or more focused understanding in what way quality may be improved is provided.

The ranking may be performed for incoming patients or patients currently being treated. The more relevant factors or attributes may be used to generate reminders or warnings to a nurse, physician, or administrator so that the particular patient more likely receives quality patient care. Similar warnings or reminders may be generated for quality scores, such as indicating patients with higher risk to fail a measure of success.

Data access may be implemented using OLAP (On-line analytical processing). Data Cubes, a data structure and functionality that allows fast access to data in a database may be used. Data Cubes may also allow manipulation and analysis using different views of the data efficiently.

FIG. 2 shows a method for ranking quality improvement factors in patient care. Various factors and/or attributes of the factors are statistically analyzed for relevance with measures of success. Any patient information may be used, such as clinical characteristics, billing, treatment, imaging, administrative and/or other information. Patient clinical characteristics may include age, gender, co-morbidities, or others. Billing includes billing codes. Treatment information may include regime, dose, time, type, medicine, or others. Imaging information may include quantifications calculated from an image. Administrative information may include physicians, nurses, departments, or other information.

The method is implemented with the system of FIG. 1, or a different system. The acts are performed in the order shown or a different order. Additional, different, or fewer acts may be provided. For example, acts 20, 22, and 24 are not provided. Acts 20, 22, and/or 24 generally correspond to creating a product for individual or separate use by different medical institutions. In another example, acts 26 and/or 28 are not provided. Acts 26 and 28 generally correspond to providing the product electronically or physically to a plurality of medical institutions.

In act 20, a computer readable media product is generated. A program or instructions are stored to generate the computer readable media product. The instructions are stored on a moveable media, such as an optical or magnetic disk, for transfer to a purchaser. Alternatively, the instructions are stored in a memory of a server for transfer over a network. In yet another embodiment, the instructions are stored in a memory of a server for application of the instructions by the server as a service.

The instructions are generated by programming, machine learning, or other approaches. For example, the instructions discussed above for FIG. 1 for operation of the processor 12 are created.

In act 22, the instructions are for measuring effect of different values in different fields (e.g., variables in a database) of a computerized medical record. A medical institution maintains a computerized medical record of patients being treated and/or previously treated. The computerized medical record includes information regarding patient care that may or may not be intuitively related to quality scores for the medical institution. The effect of the values of the variables to a success rate of quality criteria is measured. The effect may be separately determined for each of a plurality of different quality criteria. The different quality criteria are for measuring performance of the medical institution in different medical areas or for different conditions.

Any of the instructions discussed above or other instructions for determining relevance may be used. The statistical relationship of a value or variable to the measure of success is determined. The relationship is relative such that some values or variables have greater relevance, more of a desired or undesired effect on, or correlation with the result of a given measure of success. The instructions are part of a product to help medical institutions determine which factors or attributes may be worked on to most likely increase quality of care. The product may be used to identify success for reward or emulation.

In act 24, the instructions are generated for outputting the measured effect. The effect for one or more factors and/or one or more attributes are output. The output is a list, such as a ranked list, a single item, a chart associated with one or more variables or values, statistics, or other information. For example, a ranked list of variables and/or values is output. Selection of a particular variable (data field) or value may provide further information, such as a chart of the values associated with the greatest failure ratios and/or statistical information used to determine the effect.

For the ranked list, the values or variables are ordered based on the relative level of effect on a quality score, such as more effect on the failures or passes for a given quality score. Values may be particular numbers or ranges, such as two or four hour ranges in a temporal variable, may be codes, and/or may be text (e.g., yes or no, or Dr. X).

In act 26, the computer readable media product is distributed to a plurality of medical institutions. The distribution is by moveable media, network transfer, maintenance personnel install, or other mechanisms. The product is distributed as part of another software package or service or distributed as a separate product.

The medical institutions pay for the product, such as a onetime purchase, a rental, or based on usage. The product may be paid for as part of a service, such as an up charge for an automated or semi-automated chart abstraction service.

The medical institutions receive the product or access to the product for application to the computerized medical record of the medical institution. Different institutions have different medical record systems, data, and/or use different measures of quality. The product is configurable to the different medical records and different measures of quality. The relationship of the various variables and values to the scores may be different for different medical institutions regardless of similarity of scores. By distributing the product for individual use, a given medical institution may determine the effect of variables or values unique or specific to the medical institution rather than generalized information or information specific to a different institution used in a study. The application of the product is as a function of the quality criteria and computerized medical records for the respective medical institution. Different medical institutions have different success rates for the quality criteria and different computerized medical records.

In act 28, the computer readable media product is installed at the different medical institutions. The installation provides the instructions for programming the processor. Each of the medical institutions may calculate, a plurality of times, the effect of the different values on the success rates. The installation may configure the product to operate with the quality criteria and computerized medical records of the specific medical institution. In alternative embodiments, the product is installed on a server or at another location for remote processing or statistical analysis.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for ranking quality improvement factors in patient care, the system comprising:
    an input configured to receive a user selection of a quality criterion for operation of a medical facility and to receive user activation, at the medical facility, of a statistical analysis of the quality criterion;
    a computer readable media having stored therein values for a plurality of variables associated with care of a plurality of patients treated at the medical facility;
    a processor configured to determine a quality pass/fail score for each of the patients comprising an analysis of at least one of the plurality of variables for each of the patients and perform the statistical analysis, in response to the user activation, of the quality criterion as a function of the variables and the values for the variables for the patients of the medical facility, wherein the performance of the statistical analysis comprises determining a relevance of individual variables of the plurality of variables to the quality pass/fail scores across the patients of the medical facility and ranking the variables by the determined relevance; and
    a display, at the medical facility, configured to output an identification of at least a first one of the variables and at least one value for the first variable based on the ranking.

2. The system of claim 1 wherein the statistical analysis and a user interface for receiving the user activation and causing display of the identification is provided as a product for use by the medical facility, the medical facility comprising an entity for which the quality criterion is reported to another organization.

3. The system of claim 1 wherein the user activation triggers the performance by the processor periodically.

4. The system of claim 1 wherein the processor is configured to perform the statistical analysis in response to repeated user activations, some of the user activations associated with different quality criteria.

5. The system of claim 1 wherein the display is configured to display a ranked list of the variables and a ranked list of the values.

6. The system of claim 1 wherein the values and variables are stored as part of a computerized patient record system of the medical facility.

7. The system of claim 1 wherein the processor is operable to determine a trend from multiple performances of the same statistical analysis for the medical facility.

8. The system of claim 1 wherein the ranking of the variables comprises a mutual information measurement, conditional entropy measurement, or both.

9. The system of claim 1 wherein the values are ranked based on a pass/fail ratio associated with the values.

10. The system of claim 1 wherein the statistical analysis comprises a frequency table.

11. The system of claim 1 wherein the identification comprises a plurality of the values, including the one value, for the first variable, the first variable associated with a highest relevance to the quality pass/fail score, and the plurality of values associated with highest numbers of failures of the quality pass/fail score.

12. The system of claim 1 wherein the values for the variables for the patients of the medical facility are mined, at least partially, from unstructured data associated with the plurality of patients.

13. The system of claim 1 wherein the performance of the statistical analysis is not based on data from medical facilities other than the medical facility.

14. The system of claim 1 wherein the plurality of variables comprises two or more of: admitting physician, attending physician, referring physician, consulting physician, nurse status, admission time, duration of stay, discharge time, age of patient, patient type, patient status code, admitting diagnosis, or insurance.

15. The system of claim 1 wherein the plurality of variables comprises physician, admission time, and department, and wherein the values comprise physician identification for the physician variable, time of day for the admission time variable, and hospital department for the department variable.

16. The system of claim 1, wherein the performance of the statistical analysis comprises ranking the variables by effect on the quality pass/fail scores across the patients of the medical facility and ranking the values for each variable by effect on the quality pass/fail scores across the patients of the medical facility.

17. A system for ranking quality improvement factors in patient care, the system comprising:

an input configured to receive a user selection of a quality criterion for operation of a medical facility and to receive user activation, at the medical facility, of a statistical analysis of the quality criterion;

a computer readable media having stored therein values for a plurality of variables associated with care of a plurality of patients treated at the medical facility;

a processor configured to determine a quality pass/fail score for each of the patients, a quality pass score for a patient indicative of a passing score with respect to the quality criterion for that patient, and a quality fail score for a patient indicative of a failing score with respect to the quality criterion for that patient and perform the statistical analysis, in response to the user activation, of the quality criterion as a function of the variables and the values for the variables for the patients of the medical facility, wherein the performance of the statistical analysis comprises determining a relevance of individual variables of the plurality of variables to the pass/fail scores across the patients of the medical facility and ranking the variables by the determined relevance to the pass/fail scores across the patients of the medical facility; and a display, at the medical facility, configured to output an identification of at least a first one of the variables and at least one value for the first variable based on the ranking.

* * * * *